US009439845B2

(12) United States Patent
Cai et al.

(10) Patent No.: US 9,439,845 B2
(45) Date of Patent: Sep. 13, 2016

(54) GLYCYRRHETINIMIDYL HYDROXYPROLINE ALKYL ESTERS AND PROTECTED DERIVATIVES THEREOF

(71) Applicant: REVLON CONSUMER PRODUCTS CORPORATION, New York, NY (US)

(72) Inventors: Harry Cai, Skillman, NJ (US); Dariush Hosseinpour, Mason, OH (US); Alan Meyers, Flanders, NJ (US)

(73) Assignee: REVLON CONSUMER PRODUCTS CORPORATION, New York, NY (US)

( * ) Notice: Subject to any disclaimer, the term of this patent is extended or adjusted under 35 U.S.C. 154(b) by 0 days.

(21) Appl. No.: 14/771,384

(22) PCT Filed: Feb. 28, 2014

(86) PCT No.: PCT/US2014/019285
§ 371 (c)(1),
(2) Date: Aug. 28, 2015

(87) PCT Pub. No.: WO2014/134404
PCT Pub. Date: Sep. 4, 2014

(65) Prior Publication Data
US 2016/0008248 A1    Jan. 14, 2016

Related U.S. Application Data

(60) Provisional application No. 61/771,372, filed on Mar. 1, 2013.

(51) Int. Cl.
| A61K 31/40 | (2006.01) |
| C07D 207/00 | (2006.01) |
| A61K 8/49 | (2006.01) |
| A61K 45/06 | (2006.01) |
| A61K 31/375 | (2006.01) |
| A61K 31/401 | (2006.01) |
| A61K 33/32 | (2006.01) |
| A61K 33/34 | (2006.01) |
| A61K 8/67 | (2006.01) |
| A61Q 19/00 | (2006.01) |
| A61Q 19/08 | (2006.01) |
| C07J 63/00 | (2006.01) |
| A61K 8/19 | (2006.01) |
| A61Q 19/02 | (2006.01) |
| C07D 207/16 | (2006.01) |

(52) U.S. Cl.
CPC ............... *A61K 8/4913* (2013.01); *A61K 8/19* (2013.01); *A61K 8/676* (2013.01); *A61K 31/375* (2013.01); *A61K 31/40* (2013.01); *A61K 31/401* (2013.01); *A61K 33/32* (2013.01); *A61K 33/34* (2013.01); *A61K 45/06* (2013.01); *A61Q 19/005* (2013.01); *A61Q 19/007* (2013.01); *A61Q 19/02* (2013.01); *A61Q 19/08* (2013.01); *C07D 207/16* (2013.01); *C07J 63/008* (2013.01); *A61K 2800/592* (2013.01)

(58) Field of Classification Search
CPC ...................................................... C07J 63/008
USPC ......................................... 548/528; 514/423
See application file for complete search history.

(56) References Cited

U.S. PATENT DOCUMENTS 3,412,084 A * 11/1968 Turner ............... C07D 295/185
250/396 R
3,859,328 A * 1/1975 Hess ...................... A61K 31/16
560/194
2002/0009472 A1    1/2002 Takekoshi et al.

FOREIGN PATENT DOCUMENTS

| EP | 1166767 | * | 1/2002 |
| JP | 11-139951 A | | 5/1999 |
| WO | 2014/134404 A1 | | 9/2014 |

OTHER PUBLICATIONS

International Search Report and Written Opinion of the International Searching Authority issued in corresponding International Application No. PCT/US2014/019285, mailed Jun. 10, 2014 (5 pages).

* cited by examiner

*Primary Examiner* — Barbara P Badio
(74) *Attorney, Agent, or Firm* — Fitzpatrick, Cella, Harper & Scinto

(57) ABSTRACT

The present invention is directed to glycyrrhetinimidyl hydroxyproline alkyl ester compounds and their protected derivatives and cosmetically acceptable salts thereof, methods of making the compounds, cosmetic compositions containing at least one of the compounds and methods of using the same to promote collagen production in human skin. The compounds and cosmetic compositions of the invention provide various advantageous properties to the human skin.

16 Claims, No Drawings

GLYCYRRHETINIMIDYL HYDROXYPROLINE ALKYL ESTERS AND PROTECTED DERIVATIVES THEREOF

CROSS REFERENCE TO RELATED APPLICATION

The present application is a national-stage entry under 35 U.S.C. §371 of International Application No. PCT/US2014/019285, filed on Feb. 28, 2014, and claims the benefit of U.S. Provisional Application No. 61/771,372, filed Mar. 1, 2013.

BACKGROUND OF THE INVENTION

1. Field of the Invention

The present invention relates to glycyrrhetinimidyl hydroxyproline alkyl ester compounds, method of making the compounds, cosmetic compositions containing the compounds and methods of using the same to promote collagen production in human skin. The compounds and the cosmetic compositions containing such compounds provide various advantageous properties to the human skin (including hair, nail and lip). The compounds and compositions may have, among others, moisturizing and/or softening properties and would be useful for treating and/or relieving mild to moderate dry skin. The compounds and compositions may also have collagen-production inducing and skin-lightening properties. The compounds and composition may also have a correcting and perfecting benefit to sensitive skin.

2. Related Background Art

For most, if not all, having beautiful skin is very important. There are, however, challenges in achieving and maintaining beautiful skin. One of the many challenges is the exposure to the environments, e.g., sun radiation, dryness of the air, chemical (natural and/or artificial) exposure that causes damage, etc. Another challenge is aging. Both exposure to the environments and aging may cause the skin to be dry, sensitive, wrinkled or to have lines, and to lose its elasticity; they may also cause darkening/discoloration of the skin and the degradation of collagen fibers therein.

Dry skin is generally characterized by cracking, flaking, or scaling of the skin of the hands, feet, neck, face, or other parts of the body. Dry skin may result from a hereditary disorder known as ichthyosis which is a severe form of dry skin. The more common form of dry skin is a mild to moderate form of dry skin which arises due to exposure to environmental conditions of low humidity in the fall and winter seasons of the temperate climate zones. These environmental conditions give rise to, in skin areas exposed thereto, a loss of moisture from such skin areas, resulting in the formation of fissures, chaps, cracks, or flakes in the affected skin areas.

Various compounds have been proposed for use in treating or relieving dry skin. These compounds are generally formulated with other materials for topical use in the form of a lotion, cream, or ointment.

Aging causes, among others, the degradation of collagen fibers in the skin. The degradation results in the skin being flaccid and lacking firmness. Aging, generally in combination with exposure to the sun, also causes discoloration/darkening of the skin. Attempts have been made to delay, or even reverse, the effects of aging by delaying the degradation and/or increasing collagen production; or by lightening or evening out the discoloration of the skin.

There is a need for a compound that can treat and/or relieve dry skin, eczema, and restore the properties of the skin barrier. There is also a need for a compound that can delay and/or prevent the effects of aging. Further, there is a need for a stable cosmetic composition containing such a compound that provides the benefits associated with the compound.

SUMMARY OF THE INVENTION

The present invention is directed to glycyrrhetinimdyl hydroxyproline alkyl ester compounds having the following formula (I):

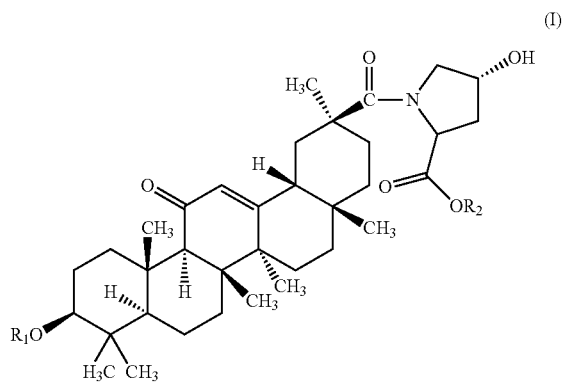

wherein $R_1$ is selected from the group consisting of H— and a protecting group and $R_2$ is a substituted or unsubstituted moiety selected from the group consisting C1 to C6 alkyl, C2 to C6 alkenyl, C2 to C6 alkynyl, aryl or heteroaryl, and the cosmetically acceptable salts thereof. The protecting group may be selected from those well-known in the art for the protection of alcohol groups and include, without limitation, from protecting groups such as acetyl, benzoyl, benzyl, beta-methoxymethyl ether, methoxymethyl ether, p-methoxy benzyl ether, methylthiomethyl ether, pivaloyl, tetrahydropyranal, trityl and silyl ether. An example of a suitable protecting group is an acetyl group.

Exemplary substituents of the $R_2$ moiety include, without limitation, hydroxyl, amino, alkoxy, alkylthio, alkylamino, arylalkyl, alkylaryl, aryl, heteroaryl, heterocycloalkyl, halogen, alkylsufinyl and alkylsulfonyl. As used herein, alkyl is a straight or branched C1-C6 saturated hydrocarbon chain; alkenyl is a straight or branched C2 to C6 unsaturated hydrocarbon chain having a single double bond; alkynyl is a straight or branched C2 to C6 unsaturated hydrocarbon chain having a single triple bond; alkoxy is a group having an oxygen atom with an alkyl group bonded thereto; aryl is a 6 carbon aromatic ring that may be substituted with 1 to 3 alkyl, hydroxyl or amino substituents; heteroaryl is an aromatic 6 membered carbon ring having as ring members one to three independently selected atoms of nitrogen, oxygen and sulfur; heterocycloalkyl is a saturated 5 to 6 membered carbon ring having as ring members one to three independently selected atoms of nitrogen, oxygen and sulfur; and halogen may be selected from a Cl, Br or F moiety.

Exemplary cosmetically acceptable salts include, without limitation, hydrochloric, malic, lactic, acetic and citric salts. The compounds of this invention have chiral centers and thus may exist in enantiomeric form. The compounds of this invention include all racemates as well as all enantiomeric forms.

The present invention includes a method of making the glycyrrhetinimidyl hydroxyproline alkyl ester compounds of formula (I) and the cosmetically acceptable salts thereof. The method of making the glycyrrhetinimidyl hydroxyproline alkyl ester compounds comprises reacting a glycyrrhetinic acid compound having the formula (II)

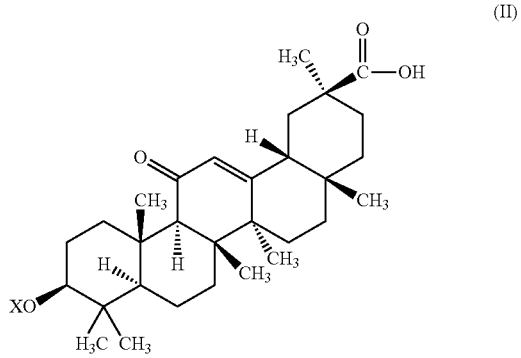

wherein X is a protecting group, with a hydroxyproline compound having the formula (III)

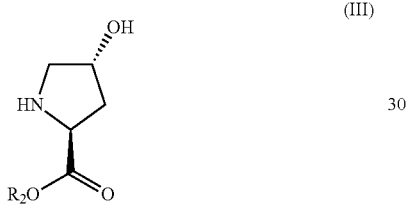

wherein $R_2$ is as previously described. The protecting group may be selected from those well-known in the art as previously exemplified. An example of a suitable protecting group is an acetyl group.

The present invention is also directed to one or more cosmetic compositions comprising up to 75% by weight of at least one of the glycyrrhetinimidyl hydroxyproline alkyl ester compounds of formula (I) or their cosmetically acceptable salts thereof. In an embodiment the glycyrrhetinimidyl hydroxyproline ester compounds of the invention are present in the cosmetic composition in an amount from about 0.001% to about 75% by weight of the cosmetic composition. The cosmetic composition may also contain one or more cosmetically acceptable carriers. Such carriers are well known.

For the purposes of the present invention, the use of the term "cosmetic composition" is understood to mean a composition suitable for application to the human body. A cosmetic composition is typically applied to the body for beautifying, cleansing, moisturizing or otherwise treating the external surface of the body, including by cleansing, coloring, conditioning, or protecting the external surface of the body part such as, for example, the skin, nails, lips, or hair. Examples of cosmetic compositions in which the present glycyrrhetinimidyl hydroxyproline alkyl ester compounds may be used includes, without limitation, skin moisturizers, sunscreens, self-tanning compositions, after-sun care compositions, makeup, protein concentrates, anti-wrinkle or anti-aging compositions, skin firming compositions, skin lightening composition, topically applied therapeutic compositions, hair care compositions, shaving preparation compositions, depilatory compositions, and cleansers.

The present invention is also directed to methods of promoting collagen production in human skin comprising the steps of applying one of the compounds of the present invention to the skin of a person, and administering a collagen release promoter to the person.

DETAILED DESCRIPTION OF THE INVENTION

The present invention is directed to a glycyrrhetinimidyl hydroxyproline alkyl ester compounds having the formula (I) and their cosmetically acceptable salts thereof.

The present invention also includes a method of making the glycyrrhetinimidyl hydroxyproline alkyl ester compounds having the formula (I) and their cosmetically acceptable salts thereof. The method of making the compounds of the invention comprises protecting the hydroxyl group of the glycyrrhetinic acid of formula (IV)

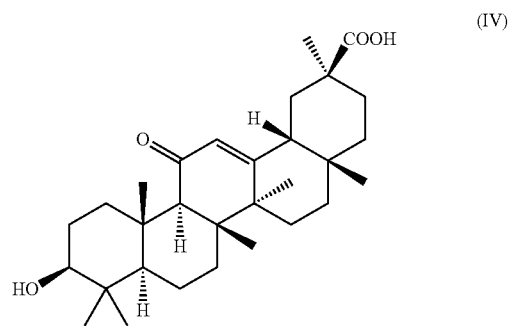

to form protected glycyrrhetinic acid of formula (II), and reacting the protected glycyrrhetinic acid of formula (II) with hydroxyproline of formula (III), as shown in scheme (I) below:

Scheme (I)

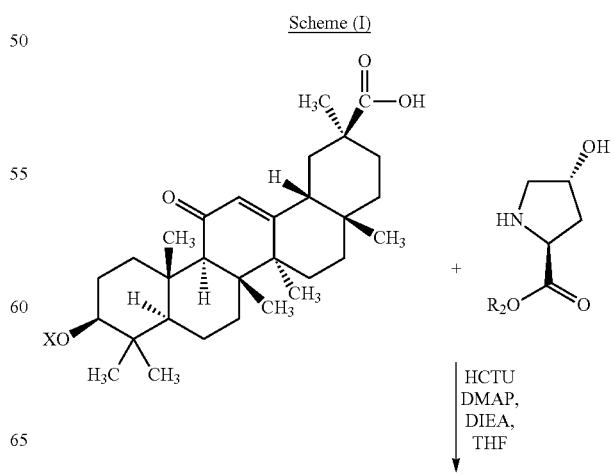

-continued

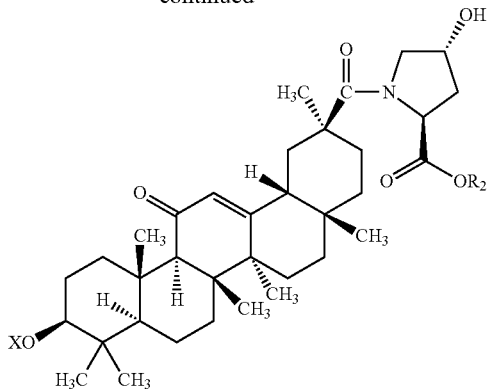

where X is a protecting group.

In one embodiment, the method includes a deprotecting step, as shown in scheme (II) below:

Scheme (II)

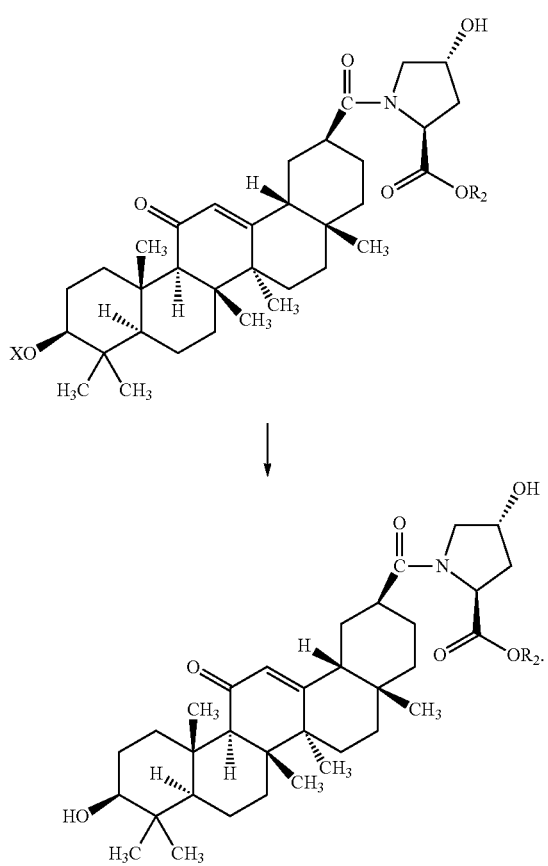

Each of the reaction products for schemes (I) and (II) may be purified or separated using standard procedures. An example of a suitable separation and purification procedure is adding the reaction product to cold water, filtering and collecting the precipitate on a Buchner funnel, and washing the solid with water.

In the method of making the glycyrrhetinimidyl hydroxyproline alkyl ester compounds of the invention, a peptide coupling reagent or activating agent may be used in the reaction. Peptide coupling agents are well known. Exemplary peptide coupling agents include 2-(6-chloro-1-H-benzotriazole-1-yl)-1,1,3,3-tetramethylaminium hexafluorophosphate ("HCTU"), dicyclohexylcarbodiimide ("DCC") and diisopropylcarbodiimide ("DIC"), 1-hydroxy-benzotriazole ("HOBt") and 1-hydroxy-7-aza-benzotriazole ("HOAt").

In the method of making the glycyrrhetinimidyl hydroxyproline alkyl ester compounds of the invention, a catalyst may be used in the reaction. Exemplary catalysts include 4-dimethylaminopyridine ("DMAP") and 2,6-di-tertiary butyl-4-dimethylaminopyridine ("DBDMAP"). A base may also be used in the reaction. An example of a suitable base is N,N-diisopropylethylamine ("DIEA"). In a preferred embodiment, equimolar amounts of catalyst, coupling agent, the compound of formula (II) and the compound of formula (III) are used and the molar amount of base used is twice the molar amount of coupling agent used. The reaction may be carried out in an organic solvent. Exemplary solvents include tetrahydrofuran ("THF"), pyridine, dichloromethane and mixtures thereof.

The substituted glycyrrhetinimidyl hydroxyproline alkyl ester compounds of the present invention possess many advantageous properties for the skin and may be useful for the treatment of various skin conditions. For example, the inventive compounds may be useful for the treatment of mild or moderate form of dry skin as it is believed to have moisturizing and/or skin-softening properties. Accordingly, the glycyrrhetinimidyl hydroxyproline alkyl ester compounds may advantageously prevent or cure the occurrence of any cracking, flaking, scaling, or chapping of the skin caused by dry skin. In addition, the substituted cyrrhetinic acid compound may be used to prevent, cure, or ameliorate acne, psoriasis, seborrhea, keratosis, diaper rash, sunburn, and windburn.

The glycyrrhetinimidyl hydroxyproline alkyl ester compounds of the invention may also be useful for the treatment, preventively or curatively, of wrinkles and/or fine lines, wizened skin, a lack of elasticity and/or of tonus of the skin, thinning of the dermis, the degradation of collagen fibers, flaccid skin, thinned skin, and the internal degradation of the skin following exposure to ultraviolet radiation.

It is believed that the glycyrrhetinimidyl hydroxyproline alkyl ester compounds of the present invention are also advantageous due to the ease of manufacture and handling thereof.

It is also believed that the glycyrrhetinimidyl hydroxyproline alkyl ester compounds of the present invention do not rapidly degrade, either in storage or formulation, resulting in a loss of activity and/or a change in color, i.e., the compounds of the present invention will be stable, have a long shelf-life. The glycyrrhetinimidyl hydroxyproline alkyl ester compound of the present invention would also have an increased penetration and permeability therefore it is more significantly absorbed by the skin to improve the condition and appearance thereof.

The present invention is also directed to methods of promoting collagen production in human skin comprising the steps of applying one of the compounds of the present invention to the skin of a person, and administering a collagen release promoter to the person. The collagen release promoter may be administered before, after or simultaneously with application of the compound to the person's skin. The collagen release promoter aides in releasing the collagen into the extracellular matrix. Exemplary collagen release promoters include Vitamin C, copper, manganese and hydroxyproline. In a preferred embodiment, the collagen release promoter is Vitamin C. In another embodiment, the compound of the present invention is in the form of a cosmetic composition. In a preferred embodiment, the cosmetic composition contains both the compound of the present invention and the collagen release promoter.

The present invention is also directed to one or more cosmetic compositions comprising up to 75% by weight of at least one of the glycyrrhetinimidyl hydroxyproline alkyl ester compounds having the formula (I) or their cosmetically acceptable salts thereof. In an embodiment, the glycyrrhetinimidyl hydroxyproline ester compound(s) of the invention are present in the cosmetic composition in an amount from about 0.001% to about 75% by weight of the cosmetic composition.

The cosmetic compositions of the present invention, which include the compound of the present invention, are useful for a variety of cosmetic purposes due to the properties mentioned above with regard to the glycyrrhetinimidyl hydroxyproline alkyl ester compounds.

In addition to the compounds of the present invention, the cosmetic compositions of the present invention may include a carrier. The carrier for use in formulating the cosmetic compositions may comprise one or more compounds which is selected based on the particular intended use of the composition. The carrier may be inorganic or organic in nature; it must be non-toxic and non-irritating. The carrier must also be compatible with the at least one glycyrrhetinimidyl hydroxyproline alkyl ester compound used in the composition.

Based on the intended use, the compositions may be care, treatment, cleansing, and/or protective products for facial or body skin; anti-wrinkle or anti-aging compositions; skin firming compositions; skin lightening compositions; compositions for irritated skin; sunscreen compositions, artificial tanning (self-tanning) compositions or after-sun care compositions; hair care and/or scalp care compositions; shaving preparation compositions; depilatory compositions; or make-up products for the skin of the face or body.

The cosmetic compositions of the present invention may also include one or more optional ingredients. Examples of the optional ingredients include but are not limited to lubricants, preservatives, perfumes, and colorants. The optional ingredients should be chemically inert with respect to each other, and with respect to the glycyrrhetinimidyl hydroxyproline alkyl ester compound.

The cosmetic compositions of the present invention may be prepared and used in the form of a lotion, cream, ointment, stick, soap, or other forms commonly employed in the art of cosmetic and skin care formulation. The compositions may be in an emulsion form.

For example, for use in treating dry skin, the cosmetic composition of the present invention may be prepared employing an effective amount (up to about 75 wt %) of the glycyrrhetinimidyl hydroxyproline alkyl ester compound of the present invention in a cosmetically acceptable carrier, e.g., a hydrophilic ointment or petrolatum. In a preferred embodiment, an amount of about 1 to about 20 wt % of the glycyrrhetinimidyl hydroxyproline alkyl ester compound is employed. In a more preferred embodiment, an amount of about 5 to about 15 wt % of the glycyrrhetinimidyl hydroxyproline alkyl ester compound is employed. It should be understood that smaller amounts of the glycyrrhetinimidyl hydroxyproline alkyl ester compound may be used in the cosmetic composition, for example, when the compound is used together with one or more other skin moisturizer or softener, or when the compound is used in cosmetic compositions that are designed primarily for other types of cosmetic functions. Examples of other skin moisturizers or softeners may include an alkoxyalkylamide compound, a ceramidyl glycyrrhizate compound and a glycyrrhetinyl glycyrrhizate compound.

When an aqueous carrier is used, the cosmetic composition may comprise about 10% to about 90% by weight of water. Preferably, the composition comprises about 10% to about 65% by weight of water. More preferably, about 10% to about 40% by weight of water, and even more preferably, about 15% to about 30% by weight of water. It should be understood however, that the water in the composition can be totally or partly eliminated by the use of non-aqueous or partially aqueous carriers.

A general non-limiting example of an aqueous composition according to the present invention is as follows:

about 0.1 to about 7 wt % emulsifying agent(s)
about 0.1 to about 15 wt % emollient(s)
about 0.1 to about 15 wt % of the compound of the present invention
about 0.1 to about 5 wt % lubricant(s)
about 0.1 to about 1 wt % preservative(s)
about 0.1 to about 1 wt % perfume(s)
about 0.01 to about 30 wt % colorant(s)
water to make up to 100 wt %.

Lists of carriers and optional ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference.

The glycyrrhetinimidyl hydroxyproline alkyl ester compounds of the present invention may be topically applied in uncompounded form to the areas of the skin to be treated therewith. Whether used as is, or in a compounded or compositional form, the glycyrrhetinimidyl hydroxyproline alkyl ester compounds of the present invention may be topically applied one or more times per day to the area of the skin to be treated for a period of time, e.g., about 7 to 30 days, in order to achieve the desired effect. More preferably, the glycyrrhetinimidyl hydroxyproline alkyl ester compound of the present invention may be applied about 1 to 2 times per day.

A makeup composition, for example, may incorporate the glycyrrhetinimidyl hydroxyproline alkyl ester compound of the present invention in a small amount, generally about 0.001 to about 10 wt %, preferably about 0.02 to about 1.0 wt % of the composition. In addition, the makeup composition may comprise about 1 to about 40 wt %, preferably about 10 to about 20 wt %, of a coloring agent in a suitable carrier. Suitable coloring agents include inorganic and organic pigments which are usable in cosmetic formulations. Examples of these pigments include carmine, bismuth oxychloride, zinc oxide, ferric oxide, ferrous oxide, kaolin, ultramarine violet, ultramarine blue, chromium oxide, chromium hydroxide, silica, manganese violet, talc, mica, and titanium oxide. The examples also include lakes of organic colorants such as FD&C Red No. 7 calcium lake, FD&C Yellow No. 5 aluminum lake, FD&C Red No. 9 barium lake, carbon black, and FD&C Red No. 30.

As used herein, "about" or "approximately" generally means within 20 percent, preferably within 10 percent, and more preferably within 5 percent of a given value or range.

Various tests may be carried out to compare formulations containing the glycyrrhetinimidyl hydroxyproline alkyl ester compound(s) of the present invention with formulations without a compound of the invention to show the advantageous properties of the glycyrrhetinimidyl hydroxyproline alkyl ester compounds. Examples of such tests are provided below:

| Property | Test(s) |
|---|---|
| Collagen synthesis stimulation | Human fibroblasts culture |
| Melanin formation inhibition | Mushroom tyrosinase; B16 melanoma cell culture |
| Anti-oxidant effect | Lipid peroxidation |
| Matrix Metalloproteinases (MMPs) inhibition | Fibroblast cell culture |
| Percutaneous absorption | Tape stripping; Bronaugh cell diffusion |
| Hydration | Dermal phase meter |

Examples set forth below show methods of making the glycyrrhetinimidyl hydroxyproline alkyl ester compounds of the present invention and its use in a cosmetic composition. The following examples are merely illustrative of the scope of the present invention and are not intended as a limitation upon the scope thereof.

Example 1

A compound of this invention was prepared by first reacting 2.35 g of glycyrrhetinic acid with 0.5 ml of acetic anhydride in 0.5 ml of pyridine to add an acetyl protecting group. The resultant acetylated glycyrrhetinic acid product was separated from the pyridine via liquid-liquid extraction using ethyl acetate. The top ethyl acetate layer was separated and the product was dried with sodium sulfate.

Next, 5 g of the acetylated glycyrrhetinic acid was mixed with 1.8 g of L-4-trans-Hydroxyproline methyl ester hydrochloride, 4.1 g of HCTU, 1.26 g of DIEA and 1.19 g of DMAP. To the mixture, three 20 ml additions of THF were added. After 24 hours, the resultant precipitate was filtered. The precipitate was mixed together with a 5% solution of potassium hydroxide and the resultant product was extracted using ethyl acetate.

Example 2

A compound of this invention was also prepared on a larger scale by first preparing a solution of 300 g of glycyrrhetinic acid dissolved in 600 ml of pyridine and 200 ml of THF. The solution was cooled to 10° C. using an ice bath. To the solution, 234.3 g of acetic anhydride was added while agitating the solution. The ice bath was then removed and the reaction proceeded overnight. Water was then added, causing the resultant acetylated glycyrrhetinic acid to precipitate. The precipitate was then dried in an oven.

Next, 138 g of acetylated glycyrrhetinic acid and 900 ml of THF were mixed to form a slurry. To the slurry, 48.73 g of L-4-trans-Hydroxyproline methyl ester hydrochloride, 110.03 g of HCTU, 69.57 g of DIEA and 32.88 g of DMAP were added. After 40 hours, the reaction product was gradually transferred to a second vessel containing ice water under agitation for crystallization. Once the transfer to the second vessel was complete, the second vessel was placed in a freezer for about 30 minutes to accelerate crystallization. The resultant precipitate was then filtered and washed several times with water. Moisture was removed from the precipitate via vacuum and then the precipitate was placed in an oven to complete drying. The final weight of the dried product was 167.5 g, indicating a 97.3% yield. HPLC showed a single major peak at 13.16 min, indicating a new product had been formed. MS/NMR results indicated the molecular weight of the resulting product was 639 g/mol.

Example 3

A cosmetic composition is prepared using the compound of Example 2. The formulation, in wt %, is as follows:

| Component | Weight % |
|---|---|
| Cyclopentasiloxane | 25.52 |
| Disteardimonium Hectorite | 1.00 |
| PEG-9 Polydimethylsiloxyethyl Dimethicone | 2.50 |
| Polyglyceryl-3 Diisostearate | 0.50 |
| Trimethylsiloxysilicate | 1.50 |
| Boron Nitride | 1.13 |
| Titanium Dioxide, Alumina, Methicone | 5.50 |
| Titanium Dioxide, Triethoxycaprylylsilane, Alumina, Silica | 5.23 |
| Iron Oxides, Methicone | 1.58 |
| 50/50 D9126I Cangee | 0.94 |
| Iron Oxides, Methicone | 0.12 |
| Mica, Methicone | 0.01 |
| Ethylhexyl Methoxycinnamate | 3.5 |
| Dimethicone, Dimethicone/PEG-10/15 crosspolymer | 4.00 |
| Dimethicone, Dimethicone crosspolymer | 2.00 |
| Phenyl Trimethicone | 1.50 |
| Phenoxyethanol | 0.70 |
| Tocopheryl Acetate | 0.01 |
| Water | 35.649 |
| Sodium Chloride | 0.50 |
| Tetrasodium EDTA | 0.01 |
| Potassium Sorbate | 0.20 |
| Pullan, Sorbitol, Trehalose, Acacia Sengal Gum | 1.25 |
| Glycerin | 3.00 |
| Glycyrrhetinimidyl hydroxyproline alkyl ester compound of Example 2 | 0.001 |
| Xanthan Gum | 0.20 |
| Laureth-7 | 0.50 |
| Caprylyl Glycol | 0.70 |
| Silica | 0.75 |
| TOTAL | 100.00 |

Example 4

It is believed that the glycyrrhetinimidyl hydroxyproline alkyl esters of the present invention are useful for promoting collagen production in human skin. In an exemplary test, normal human dermal fibroblasts (NHDF) were cultured in culture medium for 24 hours. The medium was then replaced with culture medium containing or not (control) the test compound or the reference compound (Vitamin C) or the reference mix (Vitamin C and TGF-β). The cells were then incubated for 72 hours. After incubation, the culture medium was then collected and the cells were washed and fixed. Cells were then labeled with a primary antibody (anti-collagen I or anti-collagen III). The primary antibody was then revealed using a fluorescent secondary antibody (GAR-Alexa 488) and the cell nuclei were stained Hoechst solution in parallel. An INCell Analyzer 1000 was used to take images of each well. The labeling was quantified by the measurement of the fluorescence intensity or fluorescence area normalized to the total number of cells.

The results in Tables 1 and 2 below show that the glycyrrhetinimidyl hydroxyproline methyl ester increased the NHDF's neosynthesis of collagen I by up to 26% and of collagen III by up to 42%.

TABLE 1

Total Collagen I expression in fibroblasts

| Compound | Concentration | Mean Collagen I (AU)[1] | % Control | % Stimulation |
|---|---|---|---|---|
| Control | — | 217542 | 100 | 0 |
| TGF-β + Vitamin C | 10 ng/ml + 10 μM | 271002 | 125 | 25 |
|  | 10 ng/ml + 113.5 μM | 308461 | 142 | 42 |
| Glycyrrhetinimidyl hydroxyproline methyl ester | 3.3 μM | 222721 | 102 | 2 |
|  | 10 μM | 210888 | 97 | −3 |
|  | 30 μM | 274297 | 126 | 26 |

[1]AU = fluorescence intensity/number of cells

TABLE 2

Total Collagen III expression in fibroblasts

| Compound | Concentration | Mean Collagen III (AU)[1] | % Control | % Stimulation |
|---|---|---|---|---|
| Control | — | 169463 | 100 | 0 |
| TGF-β + Vitamin C | 10 ng/ml + 10 μM | 252888 | 149 | 49 |
|  | 10 ng/ml + 113.5 μM | 401084 | 237 | 137 |
| Glycyrrhetinimidyl hydroxyproline methyl ester | 3.3 μM | 177399 | 105 | 5 |
|  | 10 μM | 199984 | 118 | 18 |
|  | 30 μM | 240374 | 142 | 42 |

However, additional results show that the NHDF treated with glycyrrhetinimidyl hydroxyproline methyl ester showed no significant increase in the extracellular release of collagen I and III, as shown in Tables 3 and 4 below. This indicates that glycyrrhetinimidyl hydroxyproline methyl ester promotes intracellular collagen production. A collagen release promoter, such as Vitamin C, could be used to release the intracellular collagen into the extracellular matrix. Note that in Tables 3 and 4 below, the apparent inhibition of glycyrrhetinimidyl hydroxyproline methyl ester on extracellular collagen fiber deposition is due to an artifact effect. Qualitative analysis of the images confirmed that there was no significant effect of the glycyrrhetinimidyl hydroxyproline methyl ester on collagen I or III extracellular fiber deposition.

TABLE 3

Extracellular Collagen I expression in fibroblasts

| Compound | Concentration | Mean Collagen I (fibers) | % Control | % Stimulation |
|---|---|---|---|---|
| Control | — | 61 | 100 | 0 |
| TGF-β + Vitamin C | 10 ng/ml + 10 μM | 62 | 101 | 1 |
|  | 10 ng/ml + 113.5 μM | 91 | 148 | 48 |
| Glycyrrhetinimidyl hydroxyproline methyl ester | 3.3 μM | 63 | 102 | 2 |
|  | 10 μM | 48 | 79 | −21 |
|  | 30 μM | 43 | 70 | −30 |

TABLE 4

Extracellular Collagen III expression in fibroblasts

| Compound | Concentration | Mean Collagen III (fibers) | % Control | % Stimulation |
|---|---|---|---|---|
| Control | — | 32 | 100 | 0 |
| TGF-β + Vitamin C | 10 ng/ml + 10 μM | 40 | 126 | 26 |
|  | 10 ng/ml + 113.5 μM | 50 | 156 | 56 |
| Glycyrrhetinimidyl hydroxyproline methyl ester | 3.3 μM | 34 | 105 | 5 |
|  | 10 μM | 34 | 107 | 7 |
|  | 30 μM | 25 | 78 | −22 |

What is claimed is:

1. A compound of formula (I):

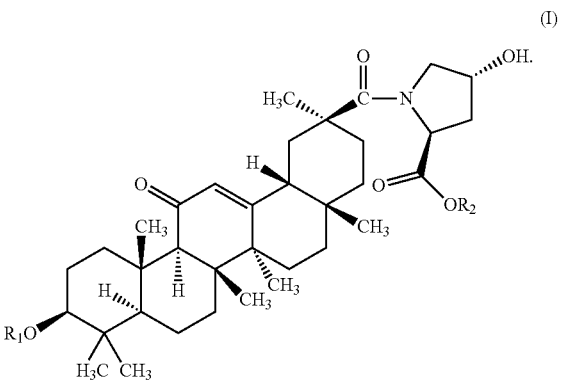

or a cosmetically acceptable salt thereof, wherein $R_1$ is selected from the group consisting of a H— and a protecting group; and $R_2$ is a substituted or unsubstituted moiety selected from the group consisting C1 to C6 alkyl, C2 to C6 alkenyl, C2 to C6 alkynyl, aryl or heteroaryl.

2. The compound of claim 1, wherein $R_1$ is H— and $R_2$ is a methyl group.

3. The compound of claim 1, wherein $R_1$ is a protecting group selected from the group consisting of acetyl, benzoyl, benzyl, beta-methoxymethyl ether, methoxymethyl ether, p-methoxy benzyl ether, methylthiomethyl ether, pivaloyl, tetrahydropyranal, trityl and silyl ether.

4. The compound of claim 1, wherein $R_1$ is a protecting group that is an acetyl group and $R_2$ is a methyl group.

5. A cosmetic composition comprising up to 75% by weight of the compound of claim 1.

6. The cosmetic composition of claim 5, wherein $R_1$ is H— and $R_2$ is a methyl group.

7. The cosmetic composition of claim 6, further comprising a cosmetically acceptable carrier and wherein the compound is in an amount of about 0.001% to about 75% by weight of the composition.

8. The cosmetic composition of claim 7, comprising a collagen release promoter.

9. A method of making a compound of formula (I):

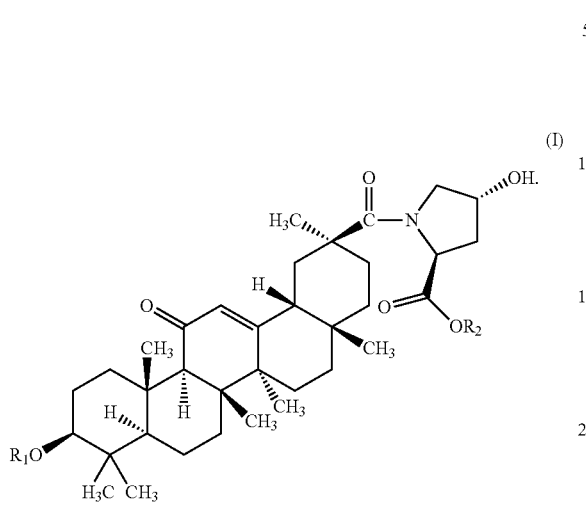

or a cosmetically acceptable salt thereof, wherein $R_1$ is selected from the group consisting of a H— and a protecting group; and $R_2$ is a substituted or unsubstituted moiety selected from the group consisting C1 to C6 alkyl, C2 to C6 alkenyl, C2 to C6 alkynyl, aryl or heteroaryl, the method comprising the steps of:

protecting glycyrrhetinic acid of formula (IV):

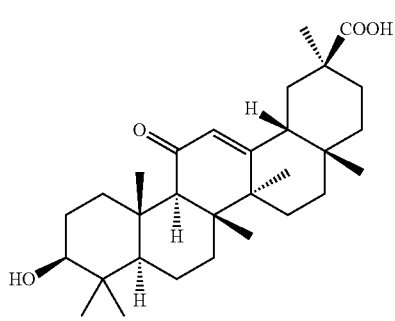

to form protected glycyrrhetinic acid of formula (II)

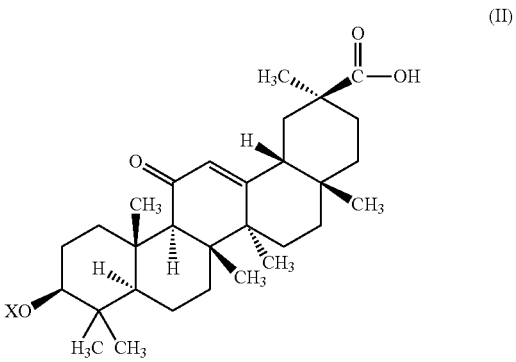

where X is a protecting group; and reacting the protected glycyrrhetinic acid of formula (II) with hydroxyproline of formula (III)

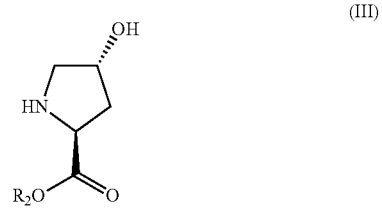

to form the protected compound of formula (I) and optionally;

deprotecting the compound of formula (I).

10. The method of claim 9, wherein the compound of formula (I) is deprotected to form the compound wherein $R_1$ is H—.

11. The method of claim 10, wherein $R_2$ is a methyl group.

12. A method of promoting collagen production in human skin comprising the steps of applying the compound of claim 1 to the skin of a person, and administering a collagen release promoter to the person.

13. The method of claim 12, wherein the collagen release promoter is selected from the group consisting of Vitamin C, copper, manganese and hydroxyproline.

14. The method of claim 12, wherein the collagen release promoter is Vitamin C.

15. The method of claim 12, wherein the compound is in the form of a cosmetic composition.

16. The method of claim 15, wherein the cosmetic composition comprises the compound and the collagen release promoter.

* * * * *

UNITED STATES PATENT AND TRADEMARK OFFICE
CERTIFICATE OF CORRECTION

PATENT NO. : 9,439,845 B2
APPLICATION NO. : 14/771384
DATED : September 13, 2016
INVENTOR(S) : Harry Cai et al.

It is certified that error appears in the above-identified patent and that said Letters Patent is hereby corrected as shown below:

In the Specification

Column 2:
Lines 13 to 27,

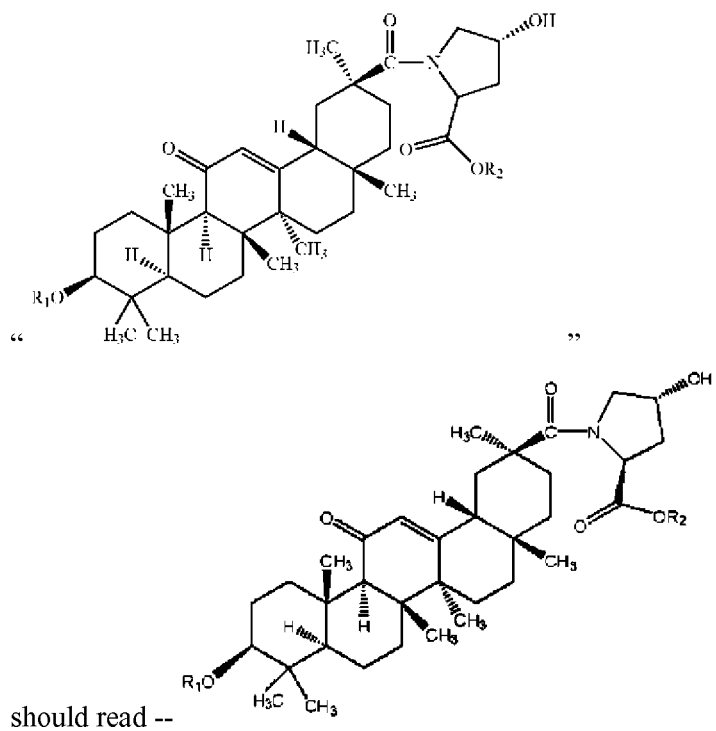

should read -- --.
Line 32, "consisting" should read --consisting of--.
Line 54, "6 membered" should read --6-membered--.
Line 56, "6" should read --6- --.

Signed and Sealed this
Twenty-fourth Day of April, 2018

Andrei Iancu
*Director of the United States Patent and Trademark Office*

CERTIFICATE OF CORRECTION (continued)
U.S. Pat. No. 9,439,845 B2

Column 4:
Line 1, "composition," should read --compositions,--.

Column 9:
Line 18, "its" should read --their--.

In the Claims

Column 12:
Line 46, "ing" should read --ing of--.

Column 13:
Line 30, "consisting" should read --consisting of--.